(12) United States Patent
Huter et al.

(10) Patent No.: US 7,842,064 B2
(45) Date of Patent: *Nov. 30, 2010

(54) HINGED SHORT CAGE FOR AN EMBOLIC PROTECTION DEVICE

(75) Inventors: Benjamin C. Huter, Murrieta, CA (US); Kevin M. Magrini, Temecula, CA (US); John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 408 days.

This patent is subject to a terminal disclaimer.

(21) Appl. No.: 11/496,854

(22) Filed: Aug. 1, 2006

(65) Prior Publication Data
US 2006/0265002 A1 Nov. 23, 2006

Related U.S. Application Data

(63) Continuation of application No. 09/944,633, filed on Aug. 31, 2001, now Pat. No. 6,592,606.

(51) Int. Cl.
*A61M 29/00* (2006.01)
(52) U.S. Cl. ..................................................... 606/200
(58) Field of Classification Search .................. 606/113, 606/114, 127, 159, 191, 200; 600/434, 585, 600/528
See application file for complete search history.

(56) References Cited

U.S. PATENT DOCUMENTS 3,952,747 A 4/1976 Kimmell, Jr.

(Continued)

FOREIGN PATENT DOCUMENTS

EP 0427429 A3 9/1991

(Continued)

OTHER PUBLICATIONS

Dilitation of the Carotid Artery by a Temporary Carotid Filter by A. Beck, St. Milic, A.M. Spagnoli, November-December Issue of OPLITAI, An International Journal on Military Medicine and Health Emergencies, pp. 67-74.

(Continued)

*Primary Examiner*—Kevin T Truong
(74) *Attorney, Agent, or Firm*—Fulwider Patton LLP; Abbott Vascular; Jonathan Feutchtwang

(57) ABSTRACT

A filtering device for capturing and removing embolic debris from a body vessel and a system for insertion and removal of the filtering device to facilitate an interventional procedure in a stenosed or occluded region of a body vessel. The filtering device is adapted to be expandable in the body vessel, allowing blood to pass therethrough while maintaining apposition with the body vessel wall and capturing embolic material released into the bloodstream during the interventional procedure, and to be collapsible to remove the captured embolic material from the body vessel. The filtering device includes a guidewire, an expandable cage assembly secured to the guide wire, filter material secured to the expandable cage assembly, and at least one hinge, the hinge allowing the expandable cage assembly to bend independent from the guide wire. The system, which includes a delivery sheath and filtering device, is adapted to retain the expandable cage assembly in a collapsed condition and deliver and deploy the filtering device at a location in the body vessel distal the treatment site.

20 Claims, 8 Drawing Sheets

U.S. PATENT DOCUMENTS

| | | | |
|---|---|---|---|
| 4,425,908 A | 1/1984 | Simon | |
| 4,494,531 A | 1/1985 | Gianturco | |
| 4,612,931 A | 9/1986 | Dormia | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,662,885 A | 5/1987 | DiPisa, Jr. | |
| 4,688,553 A | 8/1987 | Metals | |
| 4,706,671 A | 11/1987 | Weinrib | |
| 4,723,549 A | 2/1988 | Wholey et al. | |
| 4,727,873 A | 3/1988 | Mobin-Uddin | |
| 4,781,177 A | 11/1988 | Lebigot | |
| 4,790,812 A | 12/1988 | Hawkins, Jr. et al. | |
| 4,790,813 A | 12/1988 | Kensey | |
| 4,794,928 A | 1/1989 | Kletschka | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,969,891 A | 11/1990 | Gewertz | |
| 4,990,156 A | 2/1991 | Lefebvre | |
| 4,997,435 A | 3/1991 | Demeter | |
| 4,998,539 A | 3/1991 | Delsanti | |
| 5,053,008 A | 10/1991 | Bajaj | |
| 5,064,428 A | 11/1991 | Cope et al. | |
| 5,071,407 A | 12/1991 | Termin et al. | |
| 5,092,839 A | 3/1992 | Kipperman | |
| 5,100,423 A | 3/1992 | Fearnot | |
| 5,100,425 A | 3/1992 | Fischell et al. | |
| 5,102,415 A | 4/1992 | Guenther et al. | |
| 5,108,419 A | 4/1992 | Reger et al. | |
| 5,152,777 A | 10/1992 | Goldberg et al. | |
| 5,158,548 A | 10/1992 | Lau | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,383,887 A | 1/1995 | Nadal | |
| 5,421,832 A | 6/1995 | Lefebvre | |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,601,595 A | 2/1997 | Smith | |
| 5,613,981 A | 3/1997 | Boyle et al. | |
| 5,626,605 A | 5/1997 | Irie et al. | |
| 5,634,942 A | 6/1997 | Chevillon et al. | |
| 5,649,953 A | 7/1997 | Lefebvre | |
| 5,658,296 A | 8/1997 | Bates et al. | |
| 5,662,671 A | 9/1997 | Barbut et al. | |
| 5,662,703 A | 9/1997 | Yurek et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,769,816 A | 6/1998 | Barbut et al. | |
| 5,772,674 A | 6/1998 | Nakhjavan | |
| 5,776,162 A | 7/1998 | Kleshinski | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maas | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A * | 6/1999 | Tsugita et al. | 606/200 |
| 5,935,139 A | 8/1999 | Bates | |
| 5,941,869 A | 8/1999 | Patterson et al. | |
| 5,941,896 A | 8/1999 | Kerr | |
| 5,944,728 A | 8/1999 | Bates | |
| 5,954,745 A | 9/1999 | Gertler et al. | |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,013,093 A | 1/2000 | Nott et al. | |
| 6,022,336 A | 2/2000 | Zadno-Azizi et al. | |
| 6,027,520 A | 2/2000 | Tsugita et al. | |
| 6,042,598 A | 3/2000 | Tsugita et al. | |
| 6,051,015 A | 4/2000 | Maahs | |
| 6,053,932 A | 4/2000 | Daniel et al. | |
| 6,059,814 A | 5/2000 | Ladd | |
| 6,066,158 A | 5/2000 | Engelson et al. | |
| 6,074,357 A | 6/2000 | Kaganov et al. | |
| 6,086,605 A | 7/2000 | Barbut et al. | |
| 6,090,097 A | 7/2000 | Barbut et al. | |
| 6,096,053 A | 8/2000 | Bates | |
| 6,099,534 A | 8/2000 | Bates et al. | |
| 6,099,549 A | 8/2000 | Bosma et al. | |
| 6,117,154 A | 9/2000 | Barbut et al. | |
| 6,129,739 A | 10/2000 | Khosravi | |
| 6,136,015 A | 10/2000 | Kurz | |
| 6,136,016 A | 10/2000 | Barbut et al. | |
| 6,142,987 A | 11/2000 | Tsugita | |
| 6,152,946 A | 11/2000 | Broome et al. | |
| 6,152,947 A | 11/2000 | Ambrisco et al. | |
| 6,165,198 A | 12/2000 | McGurk et al. | |
| 6,165,200 A | 12/2000 | Tsugita et al. | |
| 6,168,579 B1 | 1/2001 | Tsugita et al. | |
| 6,168,604 B1 | 1/2001 | Cano | |
| 6,171,327 B1 | 1/2001 | Daniel et al. | |
| 6,171,328 B1 | 1/2001 | Addis | |
| 6,174,318 B1 | 1/2001 | Bates et al. | |
| 6,176,849 B1 | 1/2001 | Yang et al. | |
| 6,179,859 B1 | 1/2001 | Bates et al. | |
| 6,179,860 B1 | 1/2001 | Fulton, III et al. | |
| 6,179,861 B1 | 1/2001 | Khosravi et al. | |
| 6,187,025 B1 | 2/2001 | Machek | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,214,040 B1 | 4/2001 | Jayaraman | |
| 6,224,620 B1 | 5/2001 | Maahs | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,241,746 B1 | 6/2001 | Bosma et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |

| | | |
|---|---|---|
| 6,251,119 B1 | 6/2001 | Addis |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaosian |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,364,900 B1 | 4/2002 | Heuser |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Evans et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |

| Patent No. | Date | Inventor |
|---|---|---|
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boylen et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Peterson |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B2 | 8/2006 | Broome et al. |
| 7,097,651 B2 | 8/2006 | Harrison et al. |
| 7,097,834 B1 | 8/2006 | Boyle et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |

| | | |
|---|---|---|
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Satahieh et al. |
| 2003/0083692 A1 | 5/2003 | Vrba et al. |
| 2003/0083693 A1 | 5/2003 | Daniel et al. |
| 2003/0097095 A1 | 5/2003 | Brady et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0125764 A1 | 7/2003 | Brady et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0150821 A1 | 8/2003 | Bates et al. |
| 2003/0153935 A1 | 8/2003 | Mialhe |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson |
| 2003/0171803 A1 | 9/2003 | Shimon et al. |
| 2003/0176884 A1 | 9/2003 | Berrada et al. |
| 2003/0176885 A1 | 9/2003 | Broome et al. |
| 2003/0176886 A1 | 9/2003 | Daniel et al. |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosme et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Eskuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boylan et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |

| | | |
|---|---|---|
| 2004/0082697 A1 | 4/2004 | Raetzsch et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0144689 A1 | 7/2004 | Berlowitz et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boylan et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225322 A1 | 11/2004 | Garrison et al. |
| 2004/0236368 A1 | 11/2004 | McGucklin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |

| | | | |
|---|---|---|---|
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| EP | 0472334 A1 | 2/1992 |
|---|---|---|
| EP | 0533511 A1 | 3/1993 |
| EP | 1 127 556 A2 | 8/2001 |
| EP | 1 127 556 A3 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/12082 | 2/2001 |
| WO | WO01/45592 | 6/2001 |
| WO | WO01/87183 | 11/2001 |
| WO | WO02/28292 | 4/2002 |
| WO | WO2004/021928 | 3/2004 |

OTHER PUBLICATIONS

Minibasket for Percutaneous Embolectomy and Filter Protection Against Distal Embolization: Technical Note.

* cited by examiner

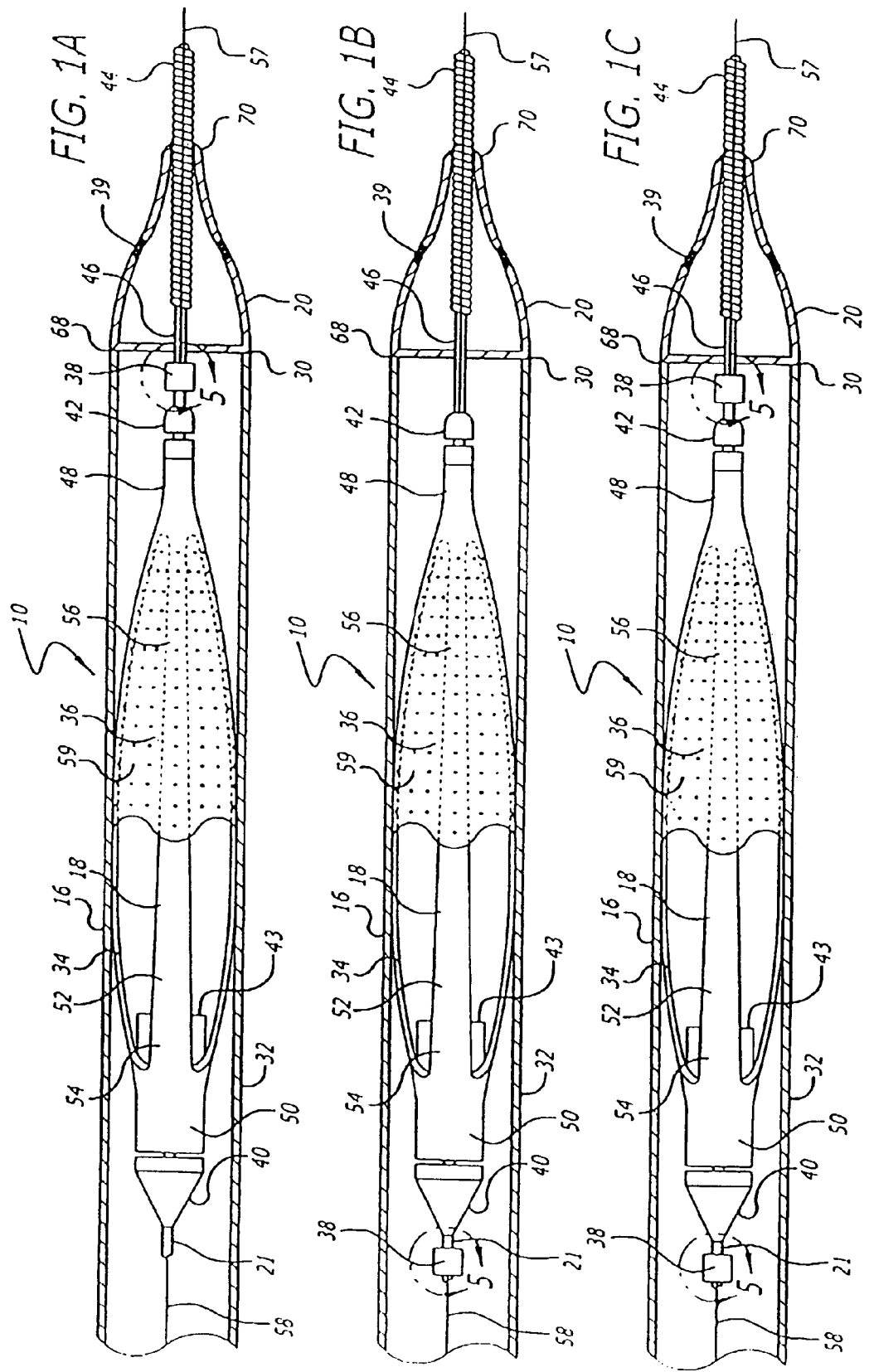

HINGED SHORT CAGE FOR AN EMBOLIC PROTECTION DEVICE

This application is a continuation of application Ser. No. 09/944,633 filed Aug. 31, 2001 now U.S. Pat. No. 6,592,606.

BACKGROUND OF THE INVENTION

The present invention relates generally to improvements in embolic protection systems and methods. In particular, the present invention relates to an improved embolic protection device and system for enabling movement thereof through a patient's tortuous vasculature to a location distal to an interventional procedure site for deployment.

A variety of non-surgical interventional procedures have been developed over the years for opening blood vessels in a patient which are stenosed or occluded by the build up of plaque or other substances on the walls of the blood vessel. Such procedures usually involve the percutaneous introduction of the interventional device into the lumen of the artery, usually through a catheter.

One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Other procedures destroy or remove the plaque build up from the walls of the blood vessel. Laser angioplasty utilizes a laser to ablate the stenosis by super heating and vaporizing the deposited plaque. Atherectomy utilizes a cutting blade which is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge elsewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed, for example, in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to address the problem of debris or fragments entering the circulatory system following treatment by one of the above-identified procedures. One approach has been to cut any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, such systems still present drawbacks since the vacuum catheter may not always remove all of the embolic material from the bloodstream and the powerful suction could cause additional damage to the patient's vasculature.

Techniques which have had some limited success include the placement of an embolic protection device such as a filter or trap downstream from the treatment site to capture embolic debris before it reaches the smaller blood vessels downstream. Such embolic protection devices are adapted to enable the capture of embolic debris which may be released into the bloodstream during the treatment, while still allowing a sufficient amount of oxygenated blood to flow past the device to supply vital organs downstream from the treatment site.

However, there have been problems associated with embolic protection devices, particularly during the expansion, deployment, and formation of the embolic protection device within the blood vessel. The deployment of an embolic protection device may not result in full expansion of the device to properly seal off the circumference of the inner wall of the blood vessel, particularly when the embolic protection device is deployed in tortuous locations having sharp bends. The length of the embolic protection device itself may result in partial collapse of its structure due to lateral loading from the sharp bend in the vessel walls, thereby causing a loss of apposition between the embolic protection device and wall. This can result in embolic material bypassing the filter.

There is a need for an improved system for treating stenosis in body vessels having sharp bends while enabling an embolic protection device to move through a patient's tortuous vasculature to a location distal to an interventional procedure site. Such a system should expand so as to efficiently and effectively seal off the entire circumference of the inner wall of the body vessel, capture embolic material, and prevent embolic material from bypassing the embolic protection device. The system should be relatively easy for a physician to use, while enabling the effective delivery and recovery of a filtering system capable of removing embolic debris released into the bloodstream. The invention disclosed herein satisfies these and other needs.

SUMMARY OF THE INVENTION

The present invention, in general, provides a filtering device for capturing and removing embolic debris from a body vessel and a system for insertion and removal of the filtering device. Embolic debris may be created during the performance of a therapeutic interventional procedure, such as a balloon angioplasty or stenting procedure. The present invention is potentially useful when performing balloon angioplasty, stenting procedures, laser angioplasty or atherectomy in critical body vessels, such as the carotid, renal, and saphenous vein graft arteries, where the release of embolic debris into the bloodstream could possibly occlude the flow of oxygenated blood to the brain or other vital organs which can cause devastating consequences to the patient.

In one aspect, the present invention includes a filtering device. The filtering device is adapted to expand against a body vessel wall to seal off the inner surface thereof, thereby preventing embolic material from bypassing the filtering device and lodging in and blocking body vessels downstream from an interventional procedure site. The filtering device is further adapted for maneuverability through tortuous anatomy having tight bends and for implantation in a curved portion of a body vessel. The present invention is potentially useful for enabling an interventional procedure to be performed in vital arteries, such as the carotid arteries, in which critical downstream body vessels can become blocked with embolic debris, including the main body vessels leading to the brain or other vital organs and in which effective implantation of an embolic protection device is often complicated by sharp bends in the body vessel. As a result, the present invention provides the physician with a higher degree of confidence in the efficient operation of the filtering device for the collection and removal of embolic debris from the body vessel when performing high-risk interventional procedures.

More particularly, the filtering device may have a pre-formed expandable shape and may include a guide wire, a pre-formed expandable basket or cage, filter material, and one or more hinges. The guide wire includes a distal end adapted to be positioned within the body vessel and to extend to a position distal to an interventional procedure site. The pre-formed expandable cage is adapted to engage the distal end of the guide wire and enables the filtering device to expand against and seal off the inner surface of a body vessel wall upon deployment. Filter material attached to the expandable cage facilitates blood flow therethrough while capturing for removal embolic debris released during an interventional procedure. The hinge provides added flexibility to allow the filtering device to be maneuvered through tortuous anatomy and to be deployed in a body vessel having sharp bends without deforming the cage.

Undeformed expansion of the expandable cage precludes the formation of a gap between the filtering device and the body vessel wall, through which embolic material may otherwise flow. The hinge facilitates maneuvering the filtering device through tortuous anatomy by allowing the cage to move independent of the guide wire while still maintaining its connection to the guide wire. Furthermore, the hinge reduces the tendency of the cage to partially collapse when deployed in a body vessel having a sharp bend due to lateral loading from the vessel walls. Moreover, the hinge ensures that the cage will maintain proper wall apposition, thereby providing effective blood filtering and embolic debris capture.

In another aspect, the present invention includes a system for delivering the filtering device through tortuous anatomy, deploying the filtering device in a body vessel at a location distal to an interventional procedure treatment site, and removing the filtering device with the captured embolic material. The system includes a delivery sheath and the aforementioned filtering device adapted to be retained in an unexpanded state by the delivery sheath. An obturator may be provided at the distal end of the guide wire to facilitate maneuvering the system in the patient's vasculature. In one configuration of the present invention, the hinge is located relative to the expandable cage to allow the cage to move independently from the axial direction defined by the portion of the guide wire which is distal to the expandable cage while still maintaining a connection between the cage and guide wire. In this manner, the hinge acts somewhat like a universal joint allowing the free articulation of the expandable cage on the guide wire to provide additional flexibility to the composite cage/guide wire, especially in tight bends in the patient's vasculature. The hinge also allows the effective length of the cage to be reduced, which helps resist the tendency of the cage to partially deform when positioned at sharp bends, thus precluding the formation of a gap between the cage and the body vessel wall. In another configuration of the present invention, a hinge is located so as to allow the cage to move independently from the axial direction defined by the portion of the guide wire which is proximal to the expandable cage while still maintaining a connection between the cage and guide wire. In still another configuration of the present invention, hinges are located so as to allow the cage to move independently from the axial directions defined by both the portion of the guide wire that is proximal to the expandable cage and the portion of the guide wire that is distal to the expandable cage while still maintaining a connection between the cage and guide wire, thereby further reducing the lateral loading on the cage due to sharp bends in the body vessel.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 1A is an elevational view, partially in section, depicting an embodiment of the present invention having a hinge at the distal side of the filtering device, the filtering device being retained in its unexpanded state by a delivery sheath;

FIG. 1B is an elevational view, partially in section, depicting an embodiment of the present invention having a hinge at the proximal side of the filtering device, the filtering device being retained in its unexpanded state by a delivery sheath;

FIG. 1C is an elevational view, partially in section, depicting an embodiment of the present invention having hinges at both the proximal and distal sides of the filtering device, the filtering device being retained in its unexpanded state by a delivery sheath;

DETAILED DESCRIPTION OF THE PREFERRED EMBODIMENTS

The present invention is directed to an improved filtering device and system for delivering, deploying, and removing the filtering device to facilitate efficient and effective performance of an interventional procedure in a body vessel. The filtering device filters the blood in the body vessel in order to pass blood therethrough while capturing embolic material released into the body vessel during the interventional procedure. Additionally, the filtering device is adapted to enable an expandable cage and filter to freely expand in the body vessel from an unexpanded state. Moreover, the filtering device facilitates placement and deployment of an expandable cage and filter in a body vessel having sharp bends without loss of apposition between the deployed cage and the vessel wall. The system is adapted to facilitate delivery and deployment of the filtering device to a location distal to an interventional procedure site. Additionally, the system is adapted to remove the filtering device and the captured embolic material from the body vessel after the interventional procedure is completed. The embodiments of the improved system are illustrated and described herein by way of example only and not by way of limitation. While the present invention is described in detail as applied to the carotid arteries of the patient, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Figure 2A:
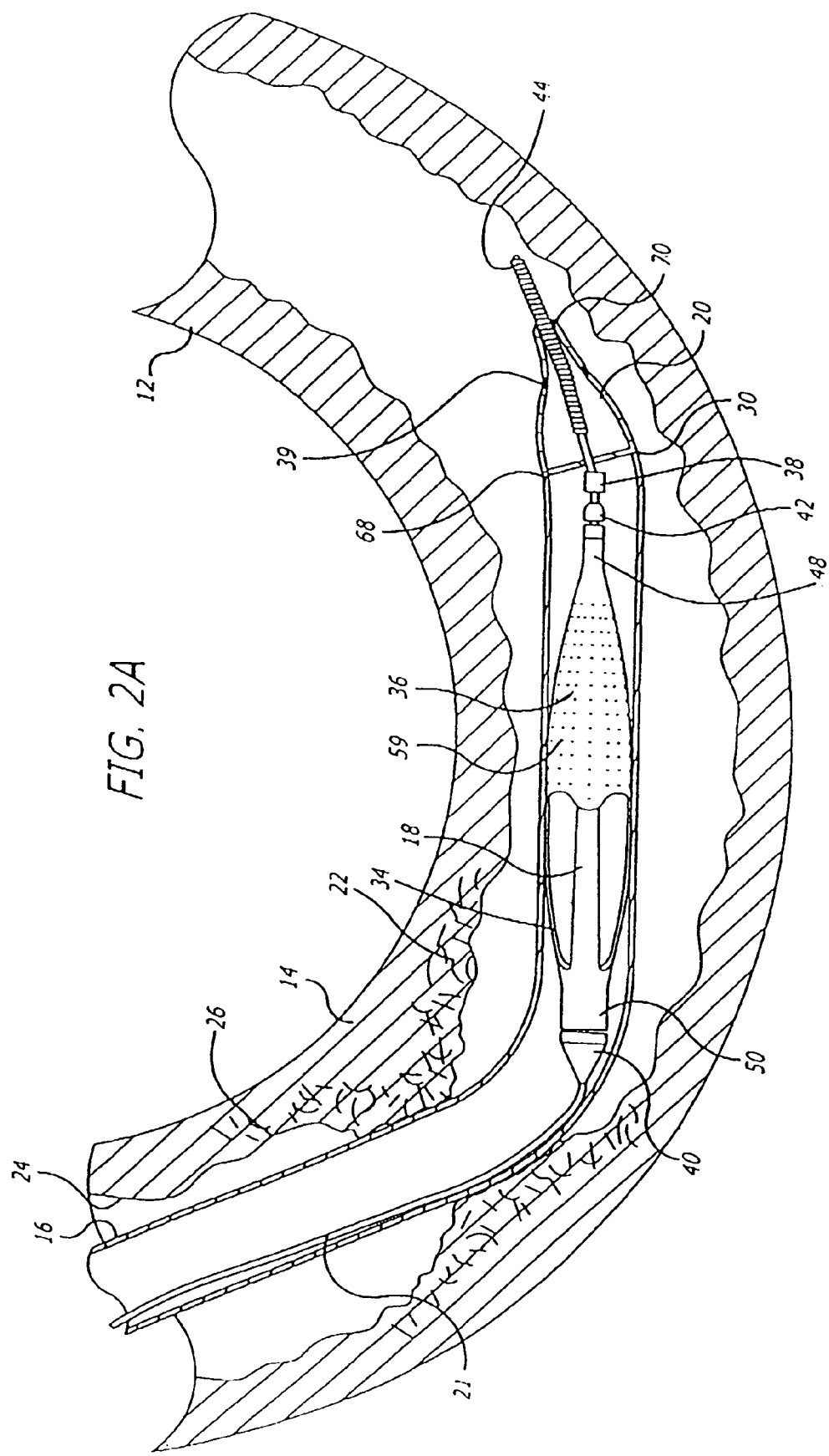
FIG. 2A is an elevational view, partially in section, showing the embodiment of the invention depicted in FIG. 1A disposed within the sharp bend of a body vessel of a patient.
Figure 2B:
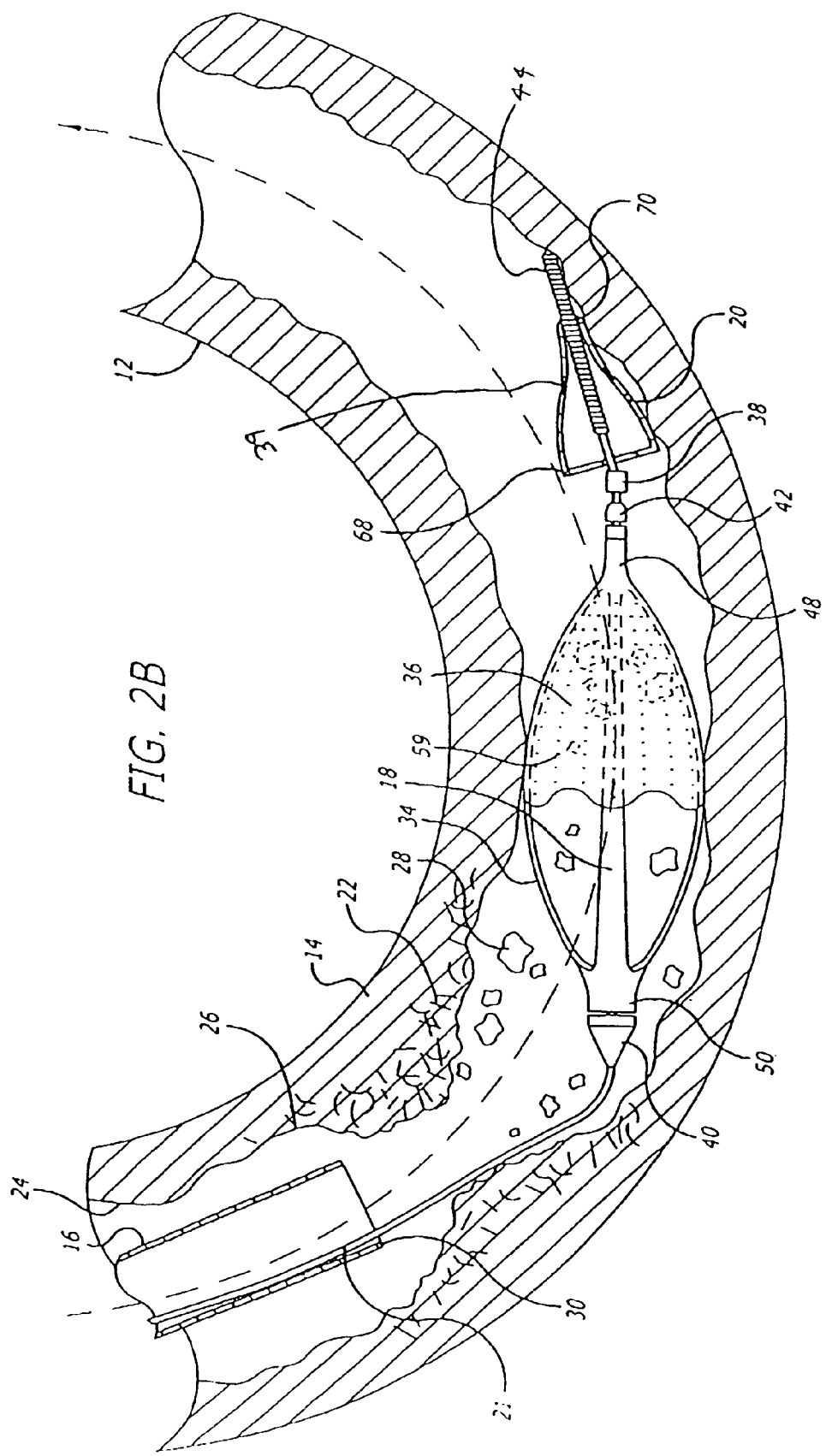
FIG. 2B is an elevational view, partially in section, showing the embodiment of the invention depicted in FIG. 1A with the delivery sheath removed and the filtering device deployed within the sharp bend of a body vessel of a patient.
Figure 3A:
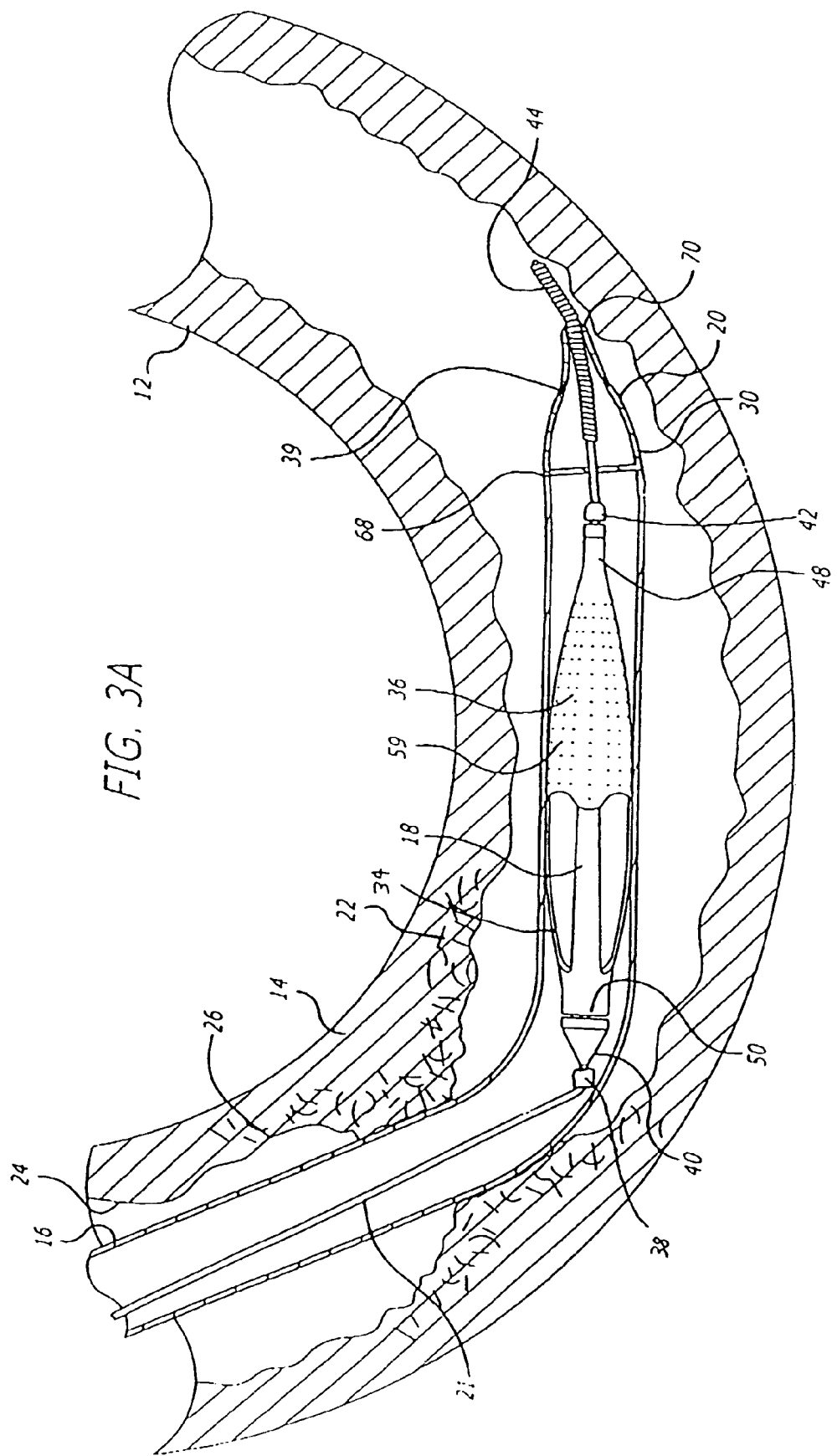
FIG. 3A is an elevational view, partially in section, showing the embodiment of the invention depicted in FIG. 1B disposed within the sharp bend of a body vessel of a patient.
Figure 3B:
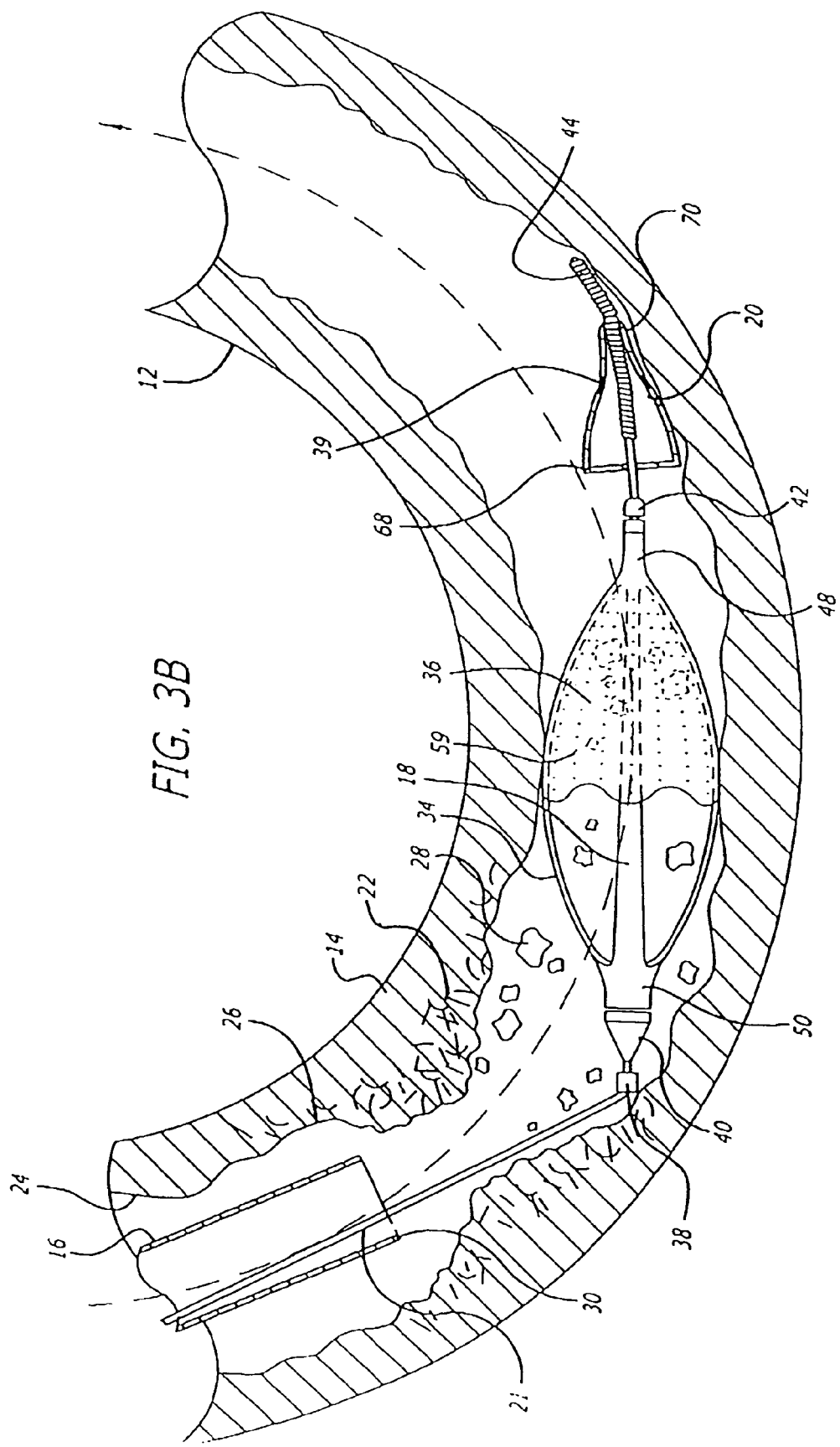
FIG. 3B is an elevational view, partially in section, showing the embodiment of the invention depicted in FIG. 1B with the delivery sheath removed and the filtering device deployed within the sharp bend of a body vessel of a patient.
Figure 4A:
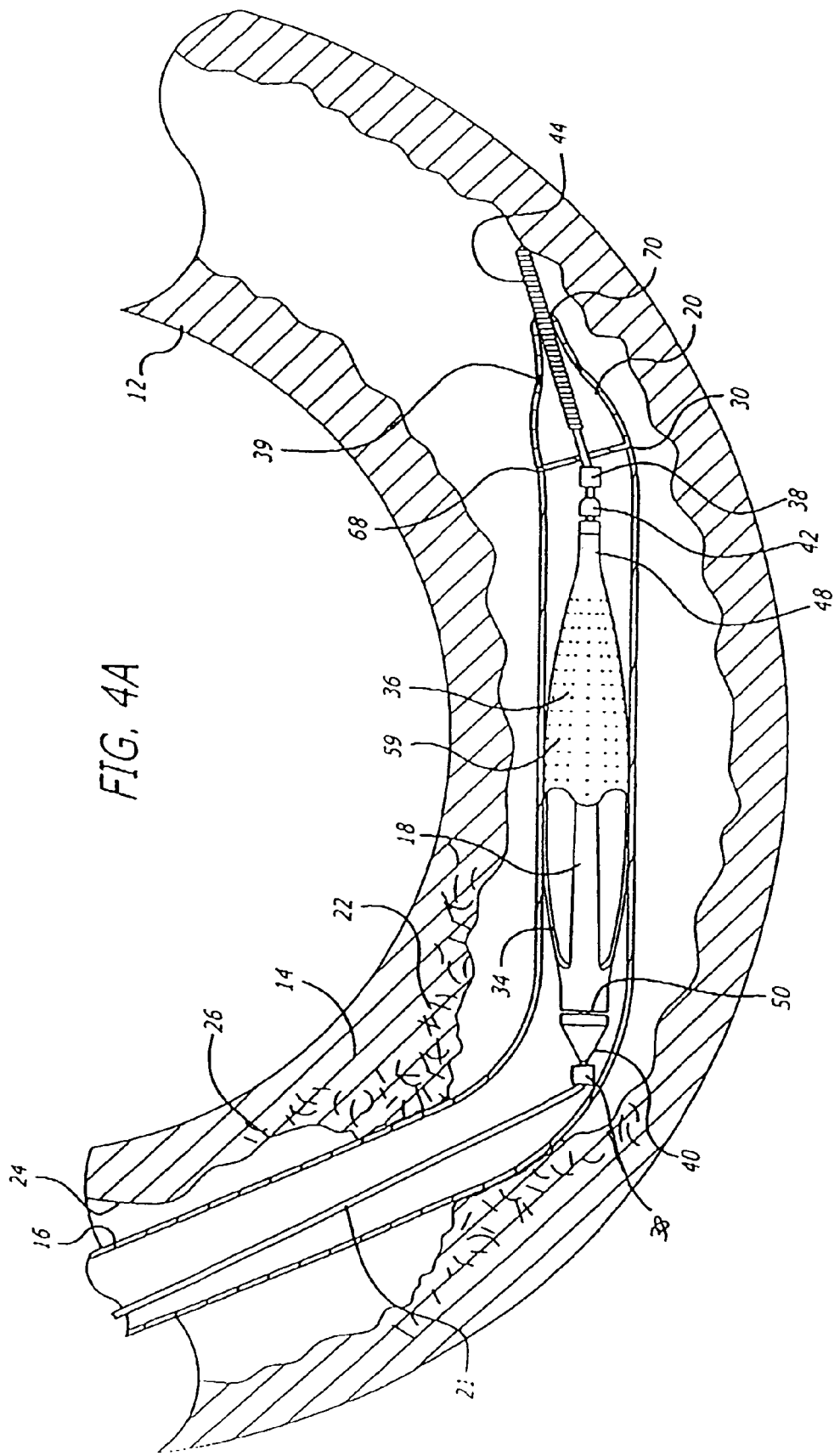
FIG. 4A is an elevational view, partially in section, showing the embodiment of the invention depicted in FIG. 1C disposed within the sharp bend of a body vessel of a patient.
Figure 4B:
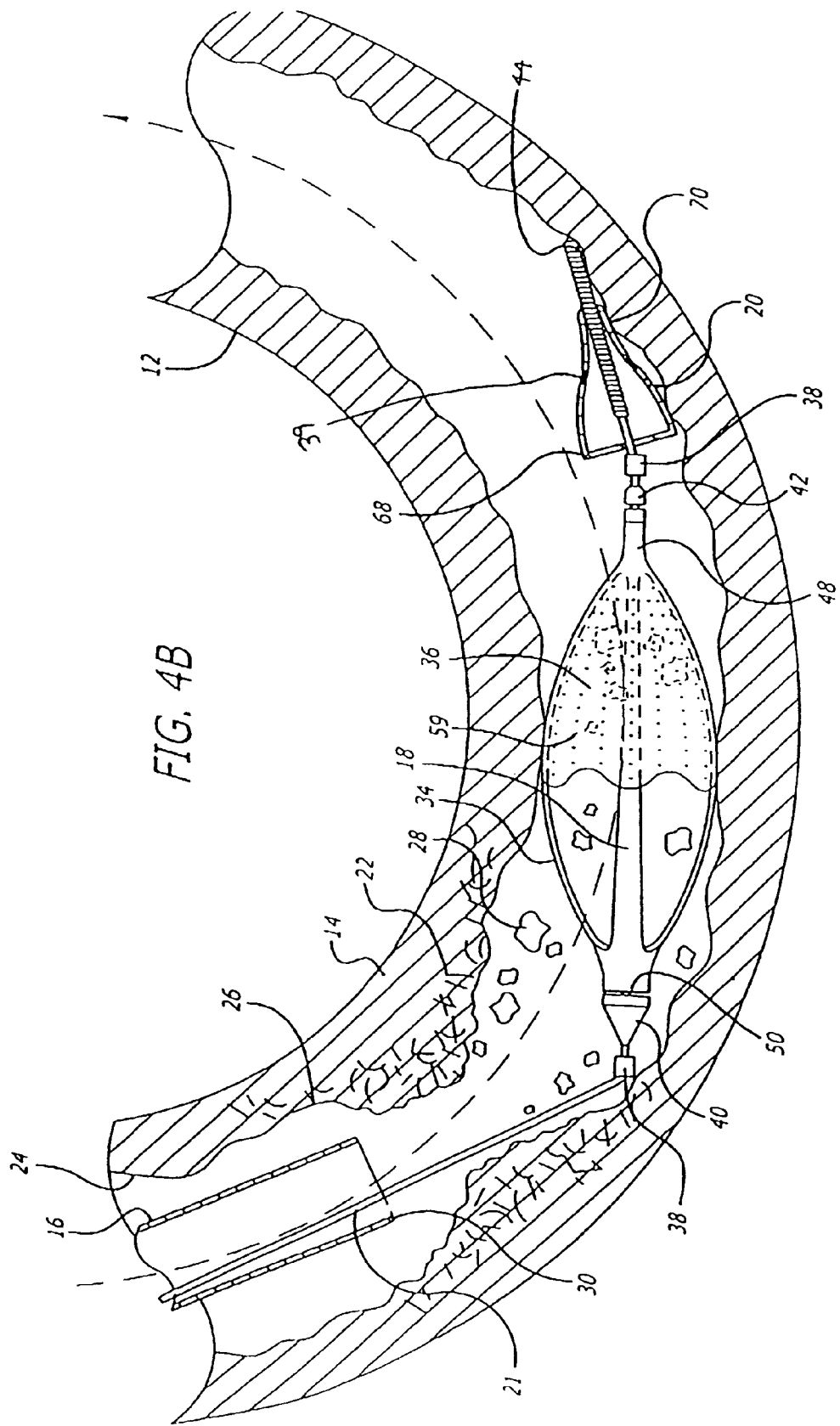
FIG. 4B is an elevational view, partially in section, showing the embodiment of the invention depicted in FIG. 1C with the delivery sheath removed and the filtering device deployed within the sharp bend of a body vessel of a patient.
Figure 5A:
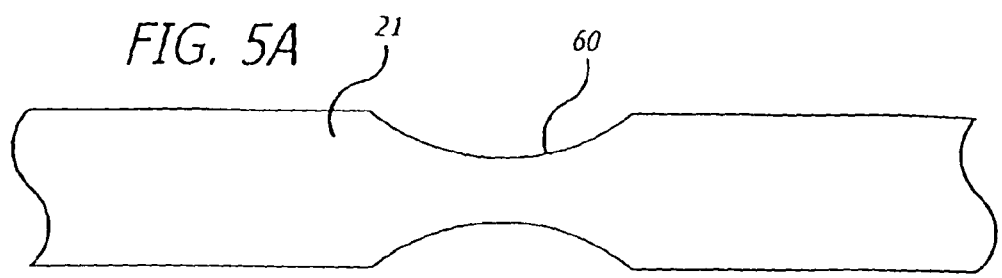
FIG. 5A is an expanded view of the area indicated by dotted lines in FIGS. 1A-1C, depicting a hinge of the present invention formed by cutting notches in the guidewire.
Figure 5B:
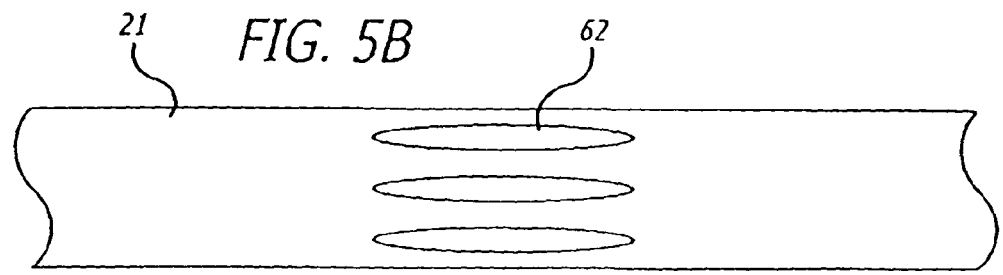
FIG. 5B is an expanded view of the area indicated by dotted lines in FIGS. 1A-1C, depicting a hinge of the present invention formed by incorporating longitudinal slots in the guidewire.
Figure 5C:
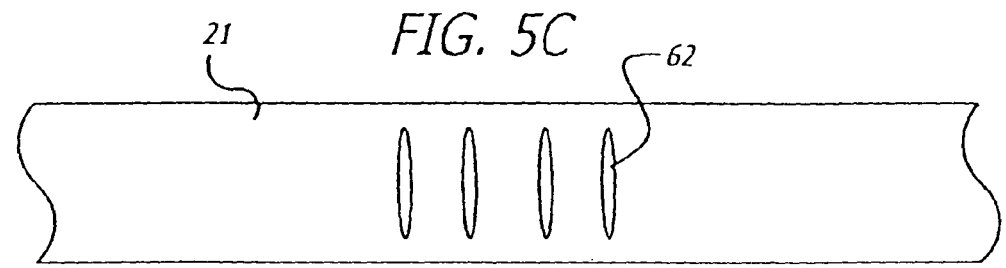
FIG. 5C is an expanded view of the area indicated by dotted lines in FIGS. 1A-1C, depicting a hinge of the present invention formed by incorporating axial slots in the guidewire.
Figure 5D:
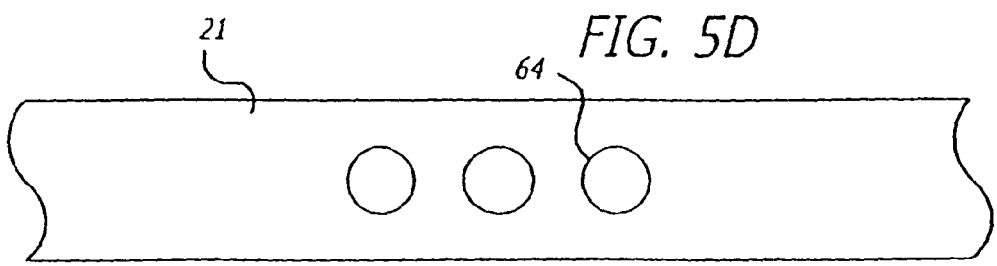
FIG. 5D is an expanded view of the area indicated by dotted lines in FIGS. 1A-1C, depicting a hinge of the present invention formed by incorporating holes in the guidewire.
Figure 5E:
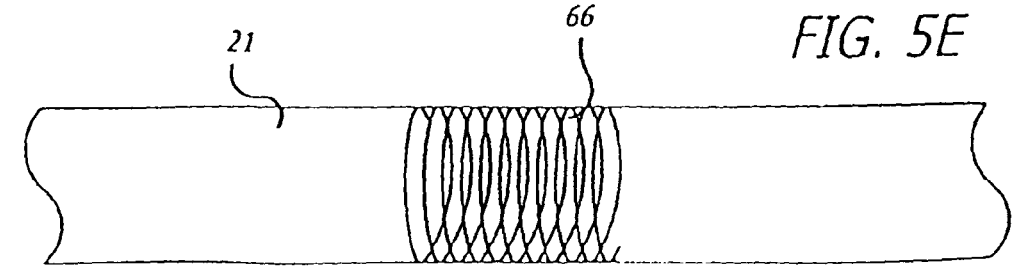
FIG. 5E is an expanded view of the area indicated by dotted lines in FIGS. 1A-1C, depicting a hinge of the present invention formed by incorporating a spring in the guidewire.

Referring to FIGS. 1A-1C, a system 10 is provided for enabling an interventional procedure to be performed in a body vessel 12. The system 10 includes a delivery sheath 16 and a filtering device 18. An obturator 20 may be provided. As shown in FIGS. 2A, 3A and 4A, the filtering device 18 may be retained in an unexpanded state by the delivery sheath 16 and guided into position within a body vessel 12 by a guide wire 21 to facilitate an interventional procedure to be performed at a treatment area 14 having a sharp bend. The treatment area 14 may comprise atherosclerotic plaque 22 which has built up against the inside wall 24 of the body vessel 12 and which decreases the diameter of the artery 26. As a result, blood flow may be diminished through this area. As shown in FIGS. 2B, 3B and 4B, once the filtering device 18 is positioned in the body vessel 12 at a point distal the area of treatment 14, the delivery sheath 16 is retracted and the filtering device 18 expands into apposition with the inside wall 24 of the body vessel 12, thereby filtering the blood flow (shown by the dotted line) and capturing embolic material 28 generated by the interventional procedure. Once the interventional procedure is completed, the filtering device 18 may be retracted into the delivery sheath 16 and the system 10 removed from the patient, thereby removing the captured embolic material 28 from the body vessel 12. Alternately, a separate recovery sheath (not shown) may be used to recover the filtering device 18.

The therapeutic interventional procedure may comprise implanting an expandable interventional instrument (not shown) to compress the build-up of plaque 22 against the inside wall 24 of a body vessel 12 of the patient, such as the carotid artery, and to increase the diameter of the occluded area 14 of the artery 26, thereby restoring sufficient blood flow to the downstream vessels leading to the brain. The expandable interventional instrument not only helps increase the diameter of the occluded area 14, but also may help prevent restenosis at the treatment area 14.

The delivery sheath 16 includes an elongated shaft 32 having a distal portion 30. The delivery sheath 16 may be formed of conventional materials of construction. Preferably, the shaft 32 is made out of a flexible material. Alternately, the shaft 32 can be made out of relatively inelastic materials such as polyethylene, polyvinyl chloride, polyesters and composite materials. The various components may be joined by suitable adhesive or cyanoacrylate based adhesives. Heat shrinking, heat bonding or laser bonding may also be employed where appropriate. Plastic-to-plastic or plastic-to-metal joints can be effected by a suitable acrylonitrile or cyanoacrylate adhesive. Variations can be made in the composition of the materials to vary properties as needed. The expandable interventional instrument may be adapted to be located in the distal portion 30 of the delivery sheath 16 for delivery and expansion at the treatment area 14.

The filtering device 18 expands within the body vessel 12, allowing blood to pass therethrough while capturing embolic material 28 released during the interventional procedure. The filtering device 18 includes a guide wire 21, expandable cage assembly 34, filter material 36, and one or more hinges 38. Stop fittings 40, 42 may be located at the proximal and distal ends of the filtering device 18. The filtering device 18 is adapted to be delivered to a position in the body vessel 12 distal the treatment area 14.

The guide wire 21 facilitates guiding the system 10 through the patient's vasculature past the treatment area 14 and may have a coiled tip 44 at the distal end 46 to provide additional flexibility. The guide wire 21 may be a single continuous piece extending through the expandable cage assembly 34. Alternately, the guide wire 21 may consist of separate distal and proximal sections, each section attached to, but not extending through, the expandable cage assembly 34, thereby reducing the tendency of the expandable cage assembly to deform in sharp bends. The guide wire 21 is typically between one-hundred thirty and three hundred centimeters long and extends two to four centimeters beyond the distal end of the filtering device 18, but it is contemplated that the invention may incorporate other guide wire 21 lengths as may be required.

The expandable cage assembly 34 has a distal end 48 and proximal end 50 which support the filter material 36 while preventing gaps between the filtering device 18 and the inside wall 24 of the body vessel 12 after deployment. The expandable cage assembly 34 is expandable to capture embolic material 28 and collapsible to retain the captured embolic material 28. The expandable cage assembly 34 is adapted to be retained in an unexpanded state by the delivery sheath 16 and expand upon retraction of the delivery sheath 16.

The expandable cage assembly 34 may include a plurality of self-expanding struts 52, each having a proximal portion 54 and a distal portion 56. It should be appreciated that this is just one particular example of an expandable cage assembly which may be used in accordance with the present invention. The expandable cage assembly 34 may be relatively flexible at the distal end 48 and relatively stiff at the proximal end 50, thereby facilitating its maneuverability in the body vessel 12 and its expansion when the delivery sheath 16 is retracted. It is contemplated that the invention may incorporate various forms of self-expanding struts known within the art. It is also contemplated that the plurality of self-expanding struts 52 may each include a radioopaque marker (not shown), thereby enabling verification of the opening or closing of the expandable cage assembly 34. It is further contemplated that the struts 52 may be made of a radioopaque material.

In one particular embodiment, the diameter of the distal end 48 of the expandable cage assembly 34 is less than the diameter of the proximal end 50 of the expandable cage assembly 34, the diameter in the unexpanded state increasing gradually along the length of the expandable cage assembly 34 from the distal end 48 to the proximal end 50. The expandable cage assembly 34 is typically one-and-one-half to three-and-one-half centimeters long and may be tubular-shaped, although it is contemplated that the invention may incorporate various sizes and shapes known within the art. The expandable cage assembly 34 may be comprised of a material, such as NITINOL, having advantageous superelasticity characteristics and which facilitates efficient formation of the expandable cage assembly 34. The expandable cage assembly 34 may be formed by heat treating or any other method known within the art. Radioopaque markers (not shown) may be comprised of platinum or gold bands or any other radioopaque material.

A proximal stop fitting 40 may be mounted on the guide wire 21 at the proximal end 50 of the expandable cage assembly 34 and a distal stop fitting 42 may be mounted on the guide wire 21 at the distal end 48 of the expandable cage assembly 34. The stop fittings 40, 42 have generally conical-shaped end portions for smooth transitions between the expandable cage assembly 34 and guide wire 21 and to provide smooth interfacing surfaces for enabling the expandable cage assembly 34 to rotate while preventing translational movement thereof. Alternately, a stop fitting 43 may be located distal to the proximal end 50 of the expandable cage assembly 34 to prevent the proximal end 50 of the cage from translating longitudinally along the guide wire while allowing the expandable cage assembly 34 to rotate freely thereon. The stop fittings 40, 42 may be secured to the guide wire 21 by a medical grade adhesive, crimping, welding, soldering, or any other method known within the art.

The filter material 36 filters the blood in the body vessel 12, allowing a sufficient amount of blood to flow while preventing embolic material 28 from passing therethrough, and may be defined by a plurality of openings 59. The filter material 36 may be parabolic-shaped, but it is contemplated that the invention can incorporate various filter material shapes known within the art. The filter material 36 may be comprised of polyurethane or any material known within the art having blood filtering capabilities. The filter material 36 may be secured either inside or outside the expandable cage assembly 34 by gluing, heat treating, or any other method known within the art.

A hinge 38 provides additional flexibility and can reduce the effective length of the expandable cage assembly 34, thereby ensuring that proper apposition with the inside wall 24 of the body vessel 12 will be maintained even if the body vessel 12 has a sharp bend. Although the guidewire 21 is flexible, the expandable cage assembly 34 of a filtering device 18 without a hinge 38 may partially collapse due to lateral loading from the body vessel 12 wall 28 when it is deployed in a body vessel 12 having a sharp bend. If the expandable cage assembly 34 partially collapses, apposition with the inside wall 24 of the body vessel 12 may be lost, thereby allowing embolic material 28 to bypass the filter material 36.

It is contemplated that a hinge 38 may be located on the guide wire 21 either at the distal end 48 of the expandable cage assembly 34 as shown in FIG. 1A, at the proximal end 50 of the expandable cage assembly 34 as shown in FIG. 1B, or in both locations as shown in FIG. 1C. These hinges 38 thus allow the distal 48 and/or proximal 50 end of the expandable cage assembly 34 to bend independently from the axial directions 57, 58 defined by the portion of the guide wire 21 that is distal to the expandable cage assembly 34 and the portion of the guide wire 21 that is proximal to the expandable cage assembly 34. This independent movement between the expandable cage assembly 34 and guide wire 21 provides added flexibility and can reduce the effective length of the expandable cage assembly 34 while still maintaining a connection between the expandable cage assembly 34 and guide wire 21. During delivery of the filtering device 18 to the treatment area 14, as shown in FIGS. 2A, 3A and 4A, the added flexibility facilitates maneuvering the system 10 through the patient's vasculature. After deployment of the filtering device 18, as shown in FIGS. 2B, 3B and 4B, the added flexibility facilitates maintaining proper apposition between the expandable cage assembly 34 and the inside wall 24 of the body vessel 12, thereby precluding embolic material 28 from bypassing the filter material 36.

FIGS. 5A-5E show various methods for implementing a hinge 38 on the guide wire 21. By cutting notches 60 (FIG. 5A), slots 62 (FIGS. 5B and 5C), holes 64 (FIG. 5D), or incorporating a spring 66 (FIG. 5E) into the guide wire 21, an area of decreased resistance to bending is created. The guide wire 21 will bend at this area of decreased resistance before additional loading is exerted on the expandable cage assembly 34. It is also contemplated that a hinge 38 may be implemented by using a portion of material of different durometer than the guide wire 21 or other methods known within the art.

The obturator 20 has an outer diameter at the proximal end 68 which is essentially the same as the outer diameter of the delivery sheath 16 and converges to an outer diameter at the distal end 70 which is slightly larger than the outer diameter of the guide wire 21. The obturator 20 is attached to the guide wire 21 such that its distal end 70 covers a portion of the of the guide wire 21 distal end 46 and its proximal end 68 lies distal of any stop fitting 42 or hinge 38 at the distal end 48 of the expandable cage assembly 34. When the filtering device 18 is retained in an unexpanded state by the introducer sheath 16, the introducer sheath 16 distal end 30 and obturator 20 proximal end 68 present a smooth profile for maneuvering the system 10 through the patient's vasculature. The obturator 20 is either partially separated from the expandable cage assembly 34 by a portion of the guide wire 21 (see FIG. 1B) or fully separated from the expandable cage assembly 34 by a hinge 38 (see FIGS. 1A and 1C), thereby allowing the obturator 20 to move independent of the expandable cage assembly 34. Therefore, the effective bending length of the filtering device 18 is further decreased and the tendency of the expandable cage assembly 34 to partially deform in sharp curves is further reduced. It is further contemplated that an obturator hinge 39 may be located on the obturator by utilizing any of the methods shown in FIGS. 5A-5E to create an area of decreased resistance along the circumference of the obturator, thereby allowing the obturator to bend.

In use, the system 10 may be positioned in the patient's vasculature utilizing any of a number of different methods known in the art. In a preferred method, the delivery sheath 16 is placed in the body vessel 12 by utilizing the guidewire 21, which is inserted into the patient's vasculature and manipulated by the physician to the treatment area 14. Once the distal end 30 of the delivery sheath 16 is located distal to the treatment area, the delivery sheath 16 is retracted, thereby allowing the expandable cage assembly 34 to expand. The expansion of the expandable cage assembly 34 is enhanced by the self-expanding struts 52 and radioopaque markers enable verification of expanding or collapsing of the expandable cage assembly 34. After the expandable cage assembly 34 is deployed distal of the treatment area 14, the interventional procedure is performed with the filter material 36 capturing embolic material 28 dislodged during the procedure. After the interventional procedure is completed, the expandable cage assembly 34 is retracted into the delivery catheter 16 or another recovery sheath (not shown), thereby causing the expandable cage assembly 34 and filter material 36, containing the captured embolic material 28, to collapse. The system 10 is then withdrawn from the patient's body vessel 12.

In view of the foregoing, it is apparent that the system and method of the present invention enhances substantially the effectiveness of performing interventional procedures, specifically in body vessels having sharp bends, by maintaining apposition between the expandable filtering device and the wall of the body vessel in which it is deployed, thereby effectively capturing embolic material created during the interventional procedure. Further modifications and improvements may additionally be made to the system disclosed herein without departing from the scope of the invention. Accordingly, it is not intended that the invention be limited, except as by the appended claims.

What is claimed:

1. A filtering device for capturing embolic material released into a body vessel during a therapeutic interventional procedure, comprising:
   a guide wire having a proximal end and a distal end and adapted to be inserted within the vasculature of a patient;
   a filter device associated with the guide wire; and
   at least one discrete hinge located on the guide wire adjacent the filter device and to allow the filter device to freely articulate on the guide wire.

2. The filtering device of claim 1, wherein:
   the at least one discrete hinge is located distal to the filter device.

3. The filtering device of claim 1, wherein:
   the at least one discrete hinge is located proximal to the filter device.

4. The filtering device of claim 1, wherein:
   the at least one discrete hinge comprises notches cut along the longitudinal axis of the guide wire such that an area of decreased guide wire diameter is created.

5. The filtering device of claim 1, wherein:
   the at least one discrete hinge comprises slots cut in the guide wire, each slot extending along the longitudinal axis.

6. The filtering device of claim 1, wherein:
   the at least one discrete hinge comprises slots cut in the guide wire, each slot extending perpendicular to the longitudinal axis.

7. The filtering device of claim 1, wherein:
   the at least one discrete hinge comprises holes cut in the guide wire along the longitudinal axis.

8. The filtering device of claim 1, wherein:
   the at least one discrete hinge comprises a spring connecting separate sections of the guide wire.

9. The filtering device of claim 1, wherein:
   the at least one discrete hinge comprises a portion of material having a different durometer than the guide wire, the portion of material connecting separate sections of the guide wire.

10. The filtering device of claim 1, further comprising:
    a discrete hinge located distal to the filter device.

11. The filtering device of claim 1, wherein:
    the filter device is generally tubular-shaped.

12. The filtering device of claim 1, wherein:
    the filter device is generally parabolic-shaped.

13. The filtering device of claim 1, wherein:
    the filter device includes an expandable cage assembly movable between an expanded position and a collapsed position and filter material attached to the cage assembly.

14. The filtering device of claim 13, wherein:
    the expandable cage assembly is relatively flexible at the distal end and relatively stiff at the proximal end.

15. A filtering device for capturing embolic material released into a body vessel during a therapeutic interventional procedure, comprising:
    a guide wire having a proximal end and a distal end and adapted to be inserted within the vasculature of a patient;
    a filter device associated with the guide wire; and
    at least one discrete hinge located on the guide wire adjacent the filter device and to allow the filter device to freely articulate on the guide wire, wherein the guide wire does not pass through the filter device and comprises separate sections, one section attached to and extending from a proximal end of the filter device and one section attached to and extending from the distal end of the filter device.

16. The filtering device of claim 15, wherein:
    the at least one discrete hinge is located distal to the filter device.

17. The filtering device of claim 15, wherein:
    the at least one discrete hinge is located proximal to the filter device.

18. The filtering device of claim 17, further comprising:
    a discrete hinge located distal to the filter device.

19. The filtering device of claim 15, wherein:
    the at least one discrete hinge comprises notches cut along the longitudinal axis of the guide wire such that an area of decreased guide wire diameter is created.

20. The filtering device of claim 15, wherein:
    the at least one discrete hinge comprises slots cut in the guide wire, each slot extending along the longitudinal axis.

* * * * *

UNITED STATES PATENT AND TRADEMARK OFFICE
CERTIFICATE OF CORRECTION

| | | |
|---|---|---|
| PATENT NO. | : 7,842,064 B2 | Page 1 of 1 |
| APPLICATION NO. | : 11/496854 | |
| DATED | : November 30, 2010 | |
| INVENTOR(S) | : Benjamin C. Huter et al. | |

It is certified that error appears in the above-identified patent and that said Letters Patent is hereby corrected as shown below:

Title page, (63), Related U.S. Application Data, delete "Continuation" insert before it --Divisional of 10/600,817 filed on Jun. 20, 2003, now Pat. No. 7,108,708, which is a continuation--.

Column 1, line 4, after the word "a" insert --divisional of 10/600,817 filed on Jun. 20, 2003, now Pat. No. 7,108,708, which is a--.

Signed and Sealed this
First Day of February, 2011

David J. Kappos
*Director of the United States Patent and Trademark Office*